(12) United States Patent
Chechik (10) Patent No.: US 8,740,769 B2
(45) Date of Patent: *Jun. 3, 2014

(54) IMPLANTABLE MEDICAL DEVICE HAVING A PALPATABLE ACTIVATION SURFACE

(71) Applicant: Coloplast A/S, Humlebaek (DK)

(72) Inventor: Joel Craig Chechik, Minneapolis, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,913

(22) Filed: May 24, 2013

(65) Prior Publication Data

US 2013/0261387 A1 Oct. 3, 2013

Related U.S. Application Data

(63) Continuation of application No. 13/425,443, filed on Mar. 21, 2012, now Pat. No. 8,491,462, which is a continuation of application No. 13/204,749, filed on Aug. 8, 2011, now Pat. No. 8,684,910.

(30) Foreign Application Priority Data

Aug. 7, 2012 (WO) ................ PCT/DK2012/000090

(51) Int. Cl.
*A61F 2/26* (2006.01)
(52) U.S. Cl.
USPC .......................................................... 600/40
(58) Field of Classification Search
USPC ................... 128/898; 600/29–32, 38, 40, 41; 606/192–195
See application file for complete search history.

(56) References Cited

U.S. PATENT DOCUMENTS

| 4,816,016 | A | 3/1989 | Schulte et al. |
| 5,101,813 | A | 4/1992 | Trick |
| 7,996,092 | B2 | 8/2011 | Mrva et al. |
| 8,491,462 | B2 * | 7/2013 | Chechik .......................... 600/40 |
| 2002/0082709 | A1 | 6/2002 | Almli et al. |
| 2007/0142700 | A1 | 6/2007 | Fogarty et al. |

FOREIGN PATENT DOCUMENTS

| DE | 3836787 | 5/1990 |
| EP | 0093507 | 11/1983 |

OTHER PUBLICATIONS

American Medical Systems, AMS 800TM Urinary Control System Operating Room Manual, 2004.
International Search Report and Written Opinion of Sep. 6, 2013 from WIPO.

* cited by examiner

*Primary Examiner* — Samuel Gilbert
(74) *Attorney, Agent, or Firm* — Coloplast Corp., Coloplast A/S; Nick Baumann (57) ABSTRACT

An implantable medical device includes an inflatable member, a reservoir, a pump attachable between the inflatable member and the reservoir and operable to move fluid from the reservoir to inflate the inflatable member, and a deflation assembly attachable between the pump and the reservoir. The deflation assembly includes a valve that selectively restricts movement of the fluid from the inflatable member to the reservoir, a base and an activation surface opposite the base. The activation surface has an outer peripheral rim surrounding a pad that is movable to displace the valve to allow the fluid to flow from the inflatable member to the reservoir. The pad is recessed relative to the outer peripheral rim such that the outer peripheral rim defines a maxima of the activation surface.

19 Claims, 8 Drawing Sheets

IMPLANTABLE MEDICAL DEVICE HAVING A PALPATABLE ACTIVATION SURFACE

BACKGROUND

An implanted penile prosthetic is effective in relieving erectile dysfunction in men.

A penile prosthetic typically includes one or more cylinders that are implanted in the corpora cavernosa of the penis, a reservoir implanted in the abdomen that communicates with the cylinder(s), and a pump located in the scrotum that is employed to move liquid from the reservoir into the cylinder(s).

In a typical application, the user squeezes a bulb of the pump multiple times to draw liquid out of the reservoir, into the bulb, and move the liquid into the cylinders. The repeated squeezing of the bulb moves the liquid from the reservoir into the cylinders, which incrementally deflates the reservoir and incrementally inflates the cylinder(s) to eventually provide the user with an erect penis. The user may return the penis to its flaccid state by activating a release mechanism associated with the pump to selectively transfer the liquid from the cylinder(s) back into the reservoir.

The above-described penile prosthetics have proven effective in relieving erectile dysfunction in men. However, there is a desire for improved penile prosthetic devices.

SUMMARY

One aspect provides a penile prosthetic that includes a cylinder, a reservoir, a pump, and a deflation assembly. The cylinder is implantable in a corpora cavernosum. The pump is attachable between the cylinder and the reservoir and is operable to move fluid from the reservoir to inflate the cylinder. The deflation assembly is attachable between the pump and the reservoir and includes a valve that selectively restricts movement of the fluid from the cylinder to the reservoir, a base and an activation surface opposite the base, where the activation surface includes an outer peripheral rim surrounding a pad that is movable to displace the valve to allow the fluid to flow from the cylinder to the reservoir. An entirety of the pad is recessed relative to the outer peripheral rim such that the outer peripheral rim defines a maxima of the activation surface.

One aspect provides a method of implanting a medical device that includes implanting an inflatable penile prosthetic into a penis of a patient, coupling the penile prosthetic to a reservoir, a pump, and a deflation assembly, where the deflation assembly is separate from the reservoir and separate from the pump. The method additionally includes implanting the deflation assembly between transversalis fascia and an exterior surface of a pelvis of the patient. The deflation assembly includes a palpatable activation surface.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The term "proximal" as employed in this application means that the referenced part is situated next to or near the point of attachment or origin or a central point: as located toward a center of the human body. The term "distal" as employed in this application means that the referenced part is situated away from the point of attachment or origin or the central point: as located away from the center of the human body. A distal end is the furthest endmost location of a distal portion of a thing being described, whereas a proximal end is the nearest endmost location of a proximal portion of the thing being described. For example, the glans penis is located distal, and of the crus of the penis is located proximal relative to the male body such that a distal end of a corpora cavernosum of the patient extends about midway into the glans penis.

"Fluid" means a non-solid substance that flows and includes gases and liquids, or a combination of a gas and a liquid.

"Gas" means a substance having molecules that disperse and are free to expand to occupy an entire volume of a container in which it is disposed. Air and methyl butane are two examples of gases.

"Liquid" means a substance having molecules that do not disperse such that the liquid resists compression and the molecules of the liquid will not disperse to fill all spaces of a container in which the liquid is disposed. Saline is an example of a liquid.

"Maxima" means the point that is a maximum distance away from a surface. In this specification, a deflation assembly provides an activation surface that includes an outer peripheral rim surrounding an activation area, and the activation area is recessed in a concave configuration relative to the outer peripheral rim such that the outer peripheral rim is a maxima of the activation surface.

Ectopic refers to the placement of a penile prosthetic deflation assembly between fascia and an exterior surface of a pelvis of the patient.

Embodiments provide a penile prosthetic having a deflation assembly that is easily identifiable to allow the patient to locate and activate (i.e., palpate) the deflation assembly. The deflation assembly is provided separately from the reservoir and separately from the pump to allow the functional aspects of the pump and the deflation assembly to be decoupled. This permits the pump to be manufactured in a smaller than usual and allows the deflation assembly to be customized based on patient anatomy.

A penile prosthetic deflation assembly is usually implanted in a scrotum of the patient, where the thin skin of the scrotum allows for easy palpation of the deflation assembly. However, some patients do not have the dexterity to operate a deflation assembly that is implanted in the scrotum.

Some penile prosthetic devices include a deflation assembly incorporated with the pump. The pump is typically implanted in the scrotum of the patient. It has been observed that the pump can rotate after it is implanted. It is difficult for the user to locate the deflation mechanism incorporated into the pump if the pump rotates. Embodiments provide a deflation mechanism that is separate from the pump where the deflation mechanism includes a prominent and easily identifiable activation surface that is even identifiable through the skin and fat tissue layers of clinically obese users.

Figure 1:
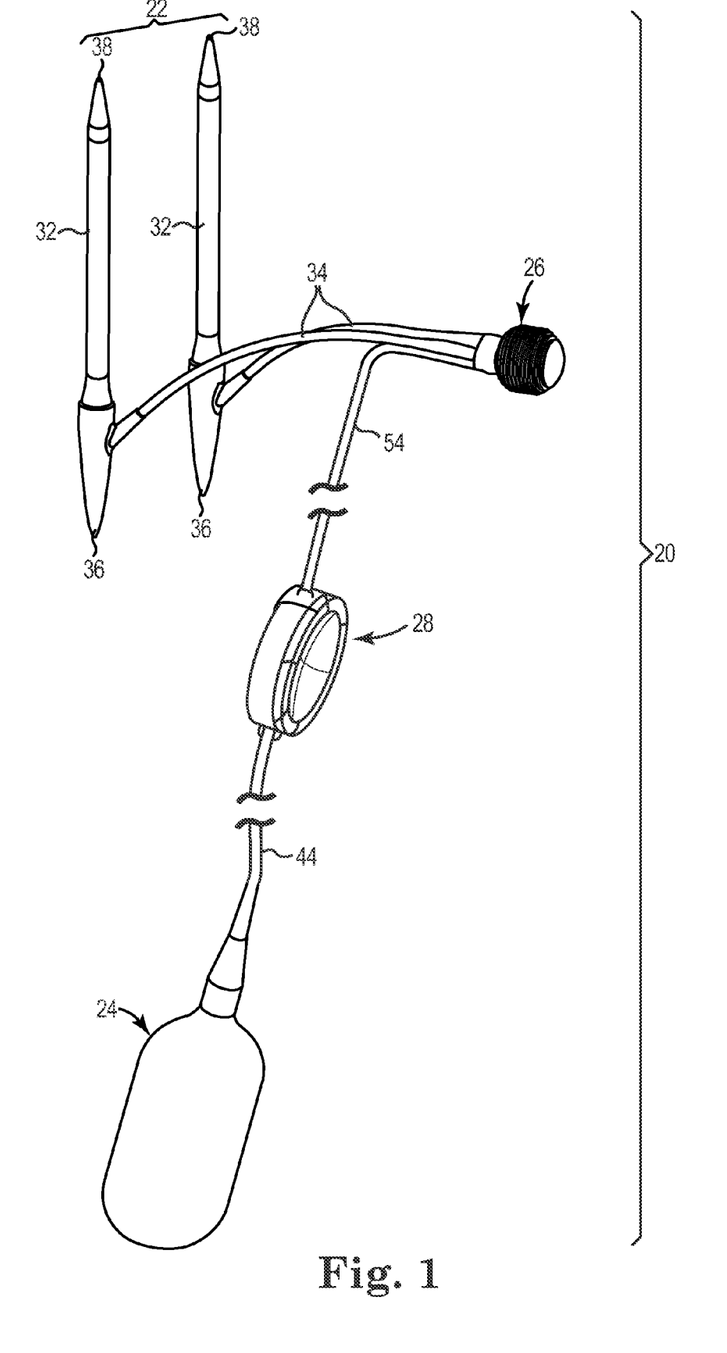
FIG. 1 is a perspective view of one embodiment of a penile prosthetic including a reservoir, a pump, and a deflation assembly separate from the reservoir and the pump.

FIG. 1 is a perspective view of one embodiment of an assembled penile prosthetic 20. The penile prosthetic 20 includes a penile implant 22, a reservoir 24, a pump 26, and a deflation assembly 28. Each of the two illustrated penile implants 22 provides a "cylinder" that is implanted in a corpora cavernosum within the shaft of the penis. The reservoir 24 retains a fluid that is employed to inflate the penile implant 22. The pump 26 is connected between the penile implant 22 and the reservoir 24 and operates to move the fluid from the reservoir 24 to the penile implant 22 to inflate the penile implant 22 to an erect state. The deflation assembly 28 functions to selectively restrict movement of the fluid from the penile implant 22 to the reservoir 24 to ensure that the penile implant 22 remains erect when inflated. In addition, the deflation assembly 28 functions to selectively move the fluid from the penile implant 22 back to the reservoir 24 to deflate the penile implant 22 to a flaccid state. The deflation assembly 28 provides a prominent activation surface (described below) that is easily palpated by the user.

In one embodiment, the penile implant 22 includes a pair of inflatable cylinders 32 that are sized to be implanted into the penis, and each of the cylinders 32 is connected to the pump 26 by tubes 34. The tubes 34 are preferably kink-resistant. Each of the cylinders 32 includes a proximal end 36 opposite a distal end 38. During implantation, the proximal end 36 (also called a rear tip) is implanted toward the crus of the penis and the distal end 38 is implanted within the glans penis. The cylinders 32 are fabricated from material configured to collapse and be flexible when the cylinders 32 are deflated to provide the penis with a comfortable flaccid state and expand when the cylinders 32 are inflated with liquid to provide the penis with an erection. Suitable material for fabricating the cylinders 32 includes silicone, polymers such as urethanes, blends of polymers with urethane, or copolymers of urethane, or the like. Suitable cylinders are available from Coloplast Corp., Minneapolis, Minn.

The reservoir 24 is sized to hold a volume of liquid between about 50-350 ml and is connected to the deflation assembly 28 by a tube 44. The tube 44 is preferably kink-resistant. In one embodiment, the reservoir 24 is provided as a cylindrical reservoir formed from an elastic, flexible polymer with a wall thickness of between 0.005-0.060 inches. In one embodiment, the reservoir 24 is provided as a "cloverleaf" style of reservoir having multiple leaves that may be folded one against the other to compactly fold the reservoir 24 for implantation into the abdomen of the user. The reservoir 24 is fabricated from material suitable for body implantation, such as silicone or the urethane-based materials described above for the cylinders 32. One suitable reservoir 24 is sized to contain approximately 130 ml of liquid and is available from Coloplast Corp., Minneapolis, Minn.

The pump 26 generally includes a bulb or other mechanism provided to move the fluid in the reservoir 24 to the penile implant 22. The pump 26 is provided with a pair of inflation ports 44 that connect with the cylinders 32 via the tubes 34 and can include one or more suitable valve assemblies configured to check or limit the flow of the fluid to the cylinders 32. The pump 26 is fabricated from material suitable for body implantation, such as silicone or the urethane-based materials described above for the cylinders 32.

The deflation assembly 28 is separate from the reservoir 24 and separate from the pump 26 and is connected between the pump 26 and the reservoir 24 by a tube 54. The tube 54 is preferably kink-resistant.

Figure 2:
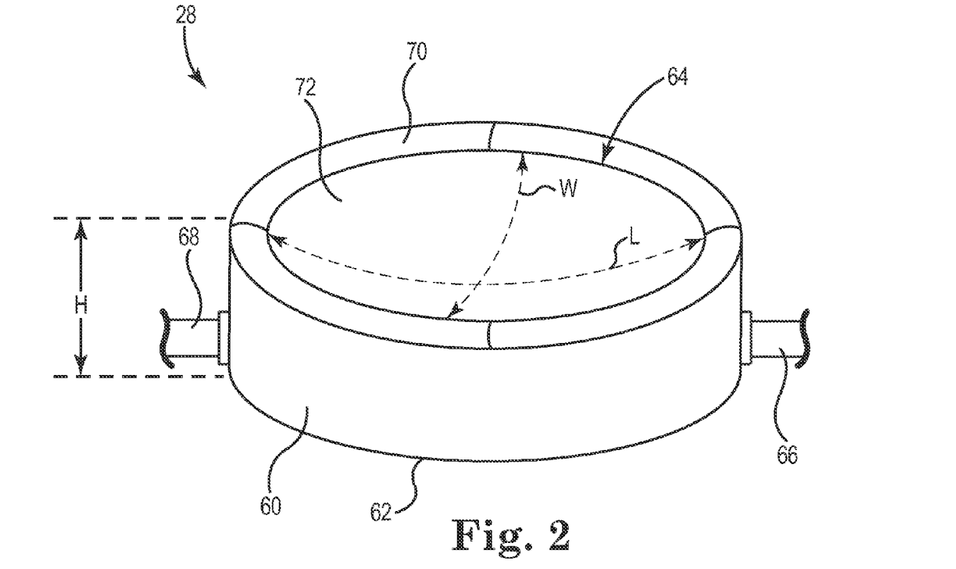
FIG. 2 is a perspective view of one embodiment of the deflation assembly illustrated in FIG. 1.
Figure 3:
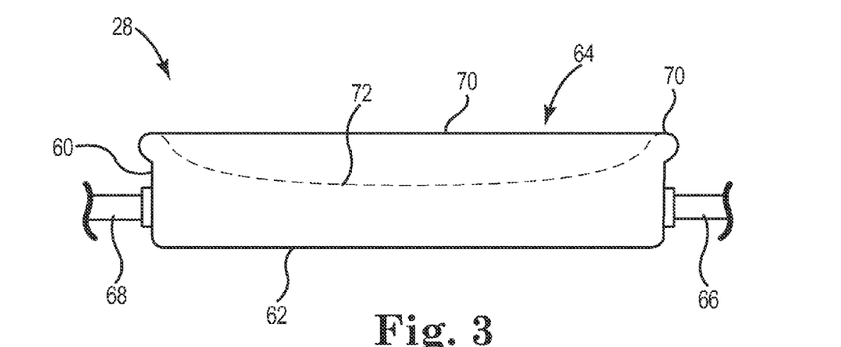
FIG. 3 is a side view of the deflation assembly illustrated in FIG. 2.
Figure 4:
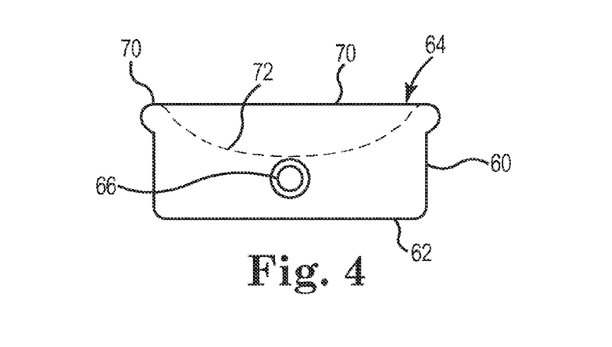
FIG. 4 is an end view of the deflation assembly illustrated in FIG. 2.

FIG. 2 is a perspective view, FIG. 3 is a side view, and FIG. 4 is an end view of one embodiment of the deflation assembly 28. The deflation assembly 28 includes a side surface 60 extending between a base 62 and activation surface 64. In one embodiment, the side surface 60 includes an inlet port 66 that communicates with the reservoir 24 and an outlet port 68 that communicates the penile implant 22 (FIG. 1). The activation surface 64 includes an outer peripheral rim 70 surrounding an activation area 72. The activation area 72 is recessed in a concave configuration relative to the outer peripheral rim 70 such that the outer peripheral rim 70 defines a maxima of the activation surface 64 (best illustrated in FIGS. 3 and 4). The activation area 72 provides a pad 72 that is central to the activation surface 64. In one embodiment, the activation area 72 (or pad 72) is entirely located between the outer peripheral rim 70 and the base 62.

The rim 70 protects the activation area 72 from unintended activation. The rim 70 is configured to be hard or immovable and easily identifiable even through skin and tissue. The rim 70 provides a landmark that once located directs the user to the location of the pad 72. The rim 70 is thus easily palpatable, but pushing on the rim 70 will not activate the deflation mechanism of the assembly 28. The pad 72 is movable and protected by the rim 70, but the pad 72 is easy to push once the rim 70 is located.

The activation area 72 is movable, and in one embodiment is fabricated from a polymer that is configured to be more flexible than the outer peripheral rim 70. In one embodiment, the outer peripheral rim 70 is harder (i.e., has a higher durometer) than the activation area 72. In one embodiment, the activation area 72 is movable and the outer peripheral rim 70 is immovable.

The deflation assembly 28 generally encloses a valve or some sort of valve assembly (FIG. 5) that is located between the inlet port 66 and the outlet port 68. The valve is provided to selectively restrict movement of the fluid from the penile implant 22 to the reservoir 24 when the penile implant 22 is erect. The activation surface 64, and in particular the activation area 72, is operable to displace the valve to allow movement of the fluid from the penile implant 22 back to the reservoir 24 to return the penile implant 22 to a flaccid state.

Figure 5:
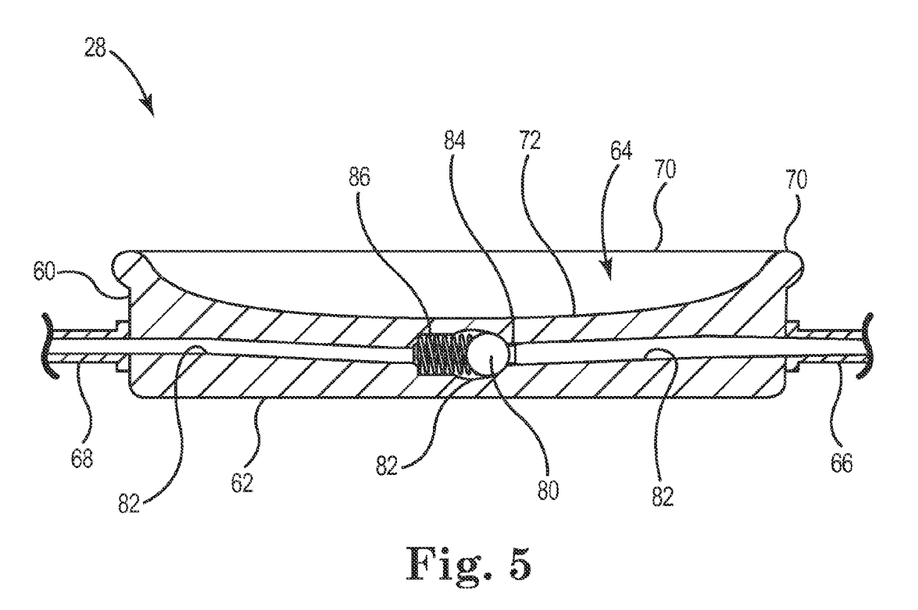
FIG. 5 is a cross-sectional view of one embodiment of the deflation assembly illustrated in FIG. 3.

In one embodiment, the activation area 72 is movable toward the base 62 to move a position of the valve. In one embodiment, the outer peripheral rim 70 is substantially immovable and provides a hard, easily palpatable surface for access by the user.

In one embodiment, the base 62 is a lower surface and the activation surface 64 is an upper surface of the deflation assembly 28. The activation surface 64 provides a length L and a width W, and the side surface 60 provides a height H. In one embodiment, the length L of the activation surface 64 is larger than the height H of the side surface 60. In one embodiment, the width W of the activation surface 64 is larger than the height H of the side surface 60. In one embodiment, the length L and the width W of the activation surface 64 are each larger than the height H a side surface 60.

FIG. 5 is a cross-sectional view of the deflation assembly 28. The deflation assembly 28 encloses a valve 80 that is disposed within a flow path 82. The flow path 82 extends between the inlet port 66 and the outlet port 68. In one embodiment, the valve 80 is a ball valve that is biased to seat against a valve seat 84 by a spring 86.

With reference to FIG. 1, when the pump 26 is repeatedly squeezed it draws fluid from the reservoir 24. The fluid drawn out of the reservoir 24 displaces the valve 80 off of the valve seat 84 to allow the fluid to flow through the flow path 82 and out of the outlet port 68 to the penile implant 22. When the suction provided by the pump 26 is reduced, for example between squeezes of the pump or when the penile implant 22 is inflated, the spring 86 forces the valve 80 against the valve seat 84 and restricts movement of the fluid from the penile implant 22 back to the reservoir 24. In one embodiment, the activation area 72 is movable and when pressed operates to displace the valve 80 off of the valve seat 84 to allow the fluid in the penile implant 22 to return to the reservoir 24, which deflates penile implant 22.

In one embodiment, the deflation assembly 28 is fabricated from polymer and integrally surrounds the valve 80, the spring 86, and the flow path 82. In one embodiment, the deflation assembly 28 is molded from silicone as a monolithic and integral unit that encloses the valve 80.

In one embodiment, the activation area 72 is provided as a diaphragm flap that extends from the rim 70, and the diaphragm flap is movable to displace the valve 80 away from the seat 84 to allow fluid to pass through the flow path 82.

Figure 6:
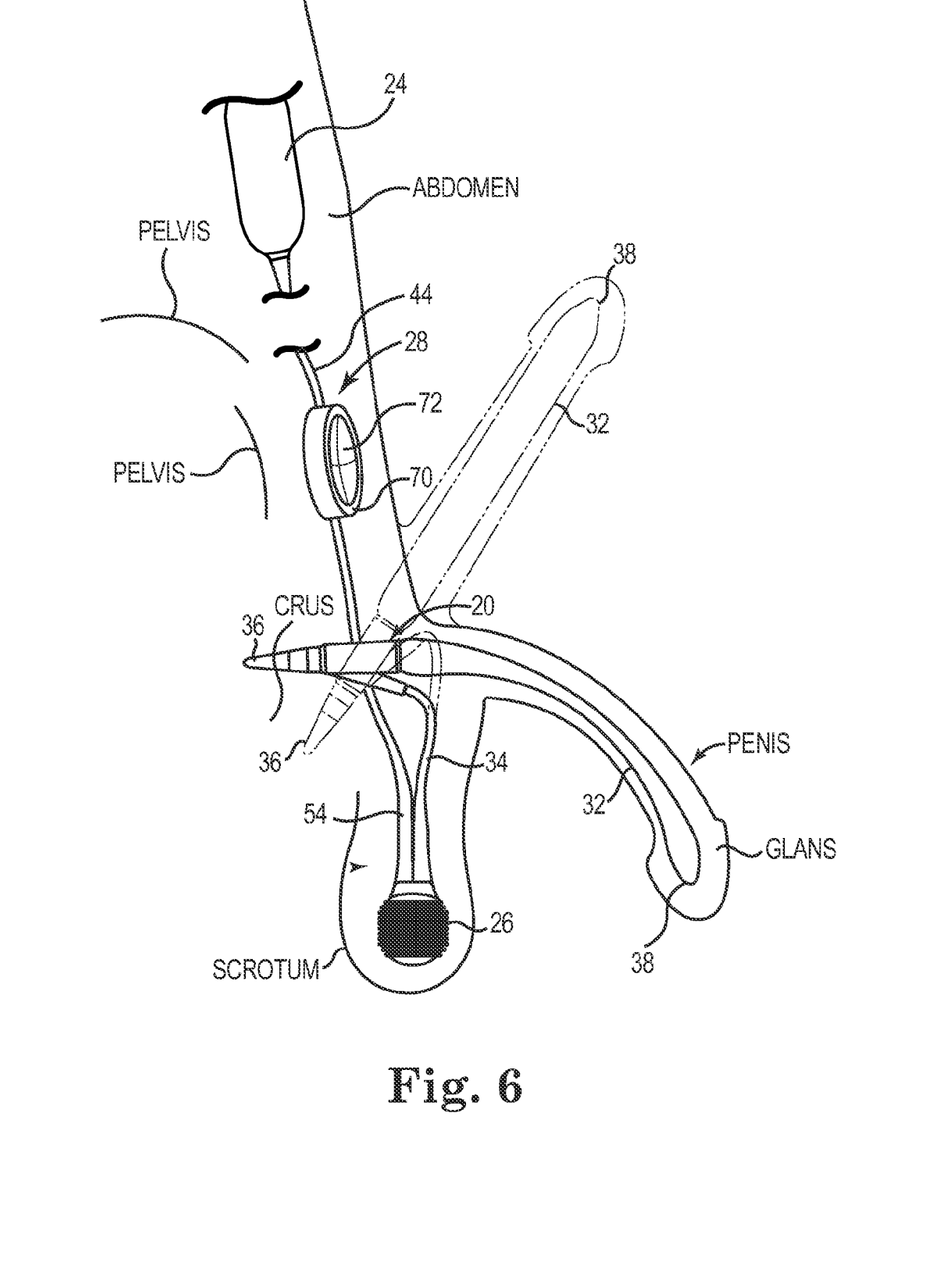
FIG. 6 is a schematic view of one embodiment of the penile prosthetic illustrated in FIG. 1 implanted in a man.

FIG. 6 is a schematic view of one embodiment of the penile prosthetic 20 implanted in a man.

The cylinders 32 are each implanted into one of adjacent corpora cavernosum of the penis with the proximal end 36 implanted into the crus of the penis and the distal end 38 implanted into the glans penis. The reservoir 24 is implanted in the abdomen, either in front of or behind the pubic bone based on the surgeon's preference. The pump 26 is implanted in the scrotum. The deflation assembly 28 is connected between the reservoir 24 and the pump 26 and is implanted under the skin in front of (i.e., exterior to) the pelvis. Suitable locations for implantation of the deflation assembly 28 include between the transversalis fascia and an exterior surface of the pelvis, or behind the puborectalis muscle of the patient. Other suitable locations for implantation of the deflation assembly 28 include placing the base 62 of the deflation assembly 28 against an iliac fossa of the pelvis, or against an iliac crest of the pelvis, or against the pelvis between an anterior gluteal line and an iliac crest of the pelvis.

During use, the pump 26 is repeatedly squeezed to draw fluid from the reservoir 24 through the deflation assembly 28 and into the cylinders 32 implanted in the penis to move the penis from a flaccid state (solid lines) to an erect state (dotted lines). The valve 80 (FIG. 5) prevents the fluid from leaving the cylinders 32 and moving back into the reservoir 24. The user presses on the activation area 72 of the deflation assembly 28 to selectively transfer the fluid in the cylinders 32 back to the reservoir 24 to move the penis from the erect state to the flaccid state. In this regard, the deflation assembly 28 is placed between transversalis fascia and an exterior surface of a pelvis of the patient and the outer peripheral rim 70 is configured to allow the patient to easily feel and locate the activation area 72.

Other existing penile prosthetic devices associate the deflation assembly with the pump that is implanted and accessible in the scrotum, or with the reservoir that is implanted and accessible in the abdomen. However, the pump implanted in the scrotum can rotate over time or through use, which can make locating the deflation assembly difficult. Likewise, the reservoir implanted in the abdomen can move or shift, which makes locating the deflation assembly difficult. In addition, some patients have additional skin folds or a layer of fatty tissue in the abdominal region, which can present challenges to the user in locating the deflation assembly. In contrast, the deflation assembly described herein provides an activation surface having an outer peripheral rim that defines a maxima of the activation surface, which makes the deflation assembly easy to palpate (locate) and use. Specifically, the outer peripheral rim 70 is configured to allow a user to palpate through the skin and fatty tissues to locate the activation area.

Some penile prosthetic devices have a "low profile" reservoir that is designed to provide a minimal depth to reduce or eliminate the visibility of the reservoir when it is implanted. For example, this style of low profile reservoir allows the reservoir to be implanted in front of the puborectalis muscle and behind the abdominal fascia in a location that is not noticeable from an external view of the patient. If such a reservoir would be modified to include a deflation assembly, the deflation assembly would likewise be hidden from view and likely difficult to locate/palpate/identify. In direct contrast, the deflation assembly described herein provides an activation surface having an outer peripheral rim that is easily identifiable when the deflation assembly is placed between transversalis fascia and an exterior surface of a pelvis of the patient.

Figure 7:
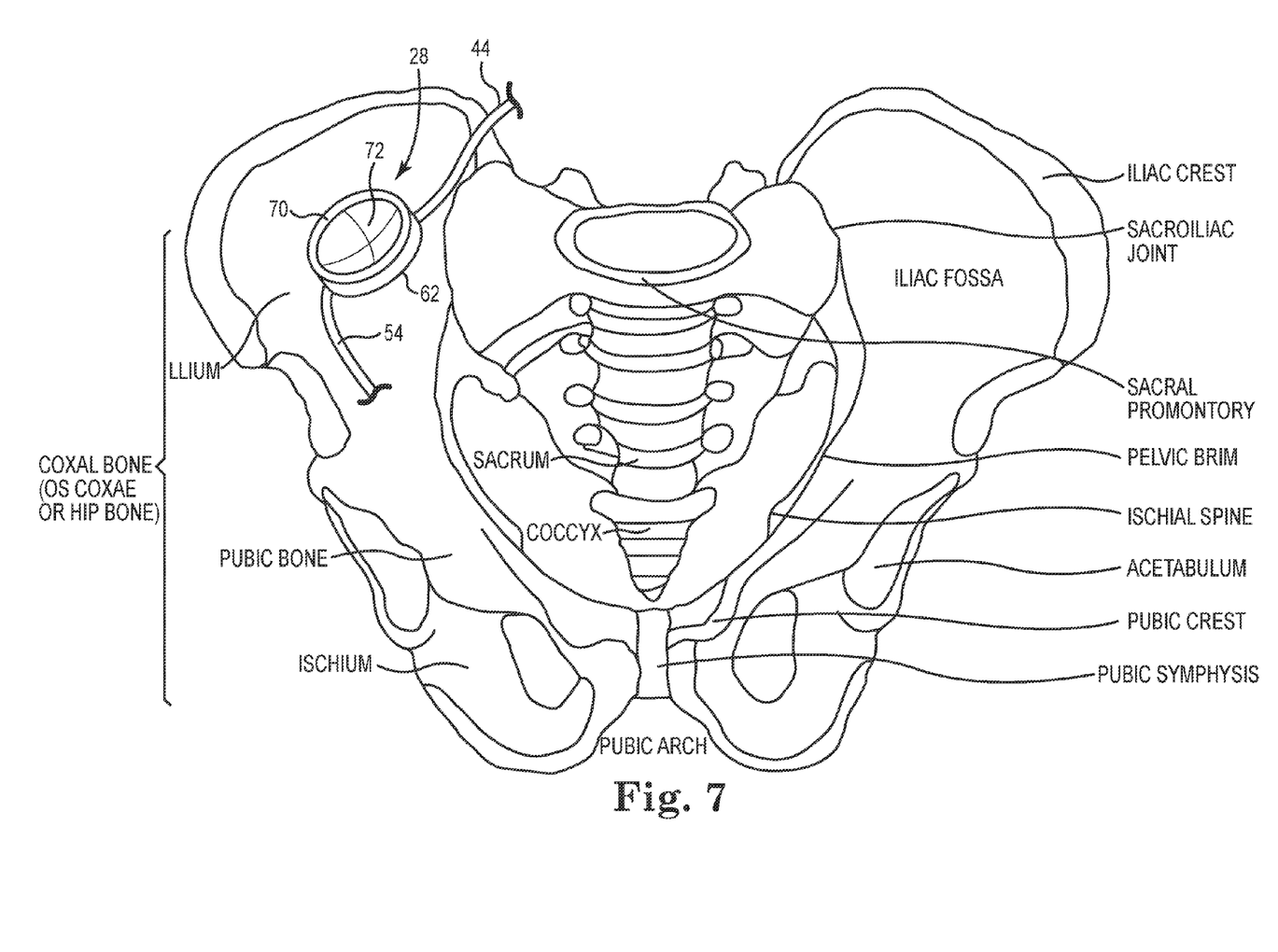
FIG. 7 is a front view of a pelvis showing the deflation assembly illustrated in FIG. 1 implanted against an iliac fossa of the pelvis.

FIG. 7 is a front view of a pelvis showing the deflation assembly 28 implanted against an iliac fossa of the pelvis. The base 62 of the deflation assembly 28 is placed against the iliac fossa with the tube 44 extending to the reservoir 24 and the tube 54 extending to the pump 26. In this location, the deflation assembly 28 is located between the transversalis fascia and an exterior surface of the pelvis. The base 62 is thus placed against the hard surface of the iliac fossa and the outer peripheral rim 70 is easy to locate, which makes the activation area 72 easily palpatable.

Figure 8:
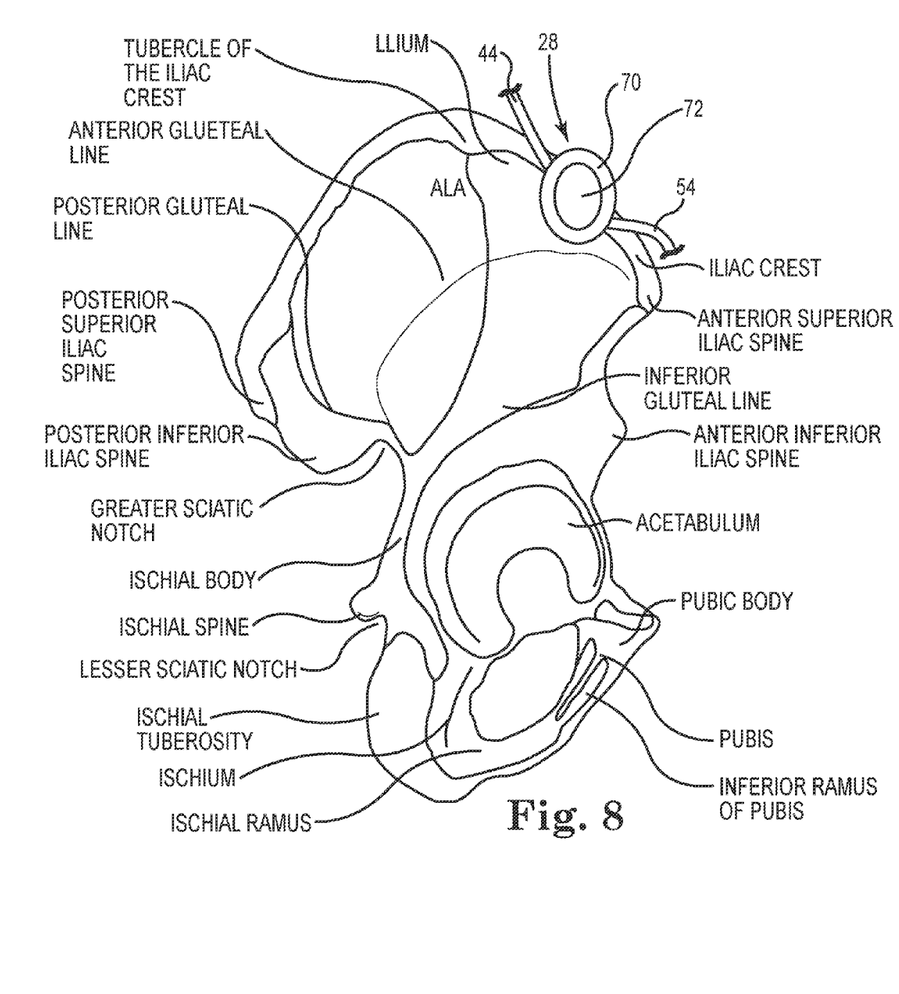
FIG. 8 is a side view of a pelvis showing the deflation assembly illustrated in FIG. 1 implanted against an iliac crest of the pelvis.

FIG. 8 is a side view of a pelvis showing the deflation assembly 28 implanted against an iliac crest of the pelvis. The base 62 of the deflation assembly 28 is located against the iliac crest with the tube 44 extending to the reservoir 24 and the tube 54 extending to the pump 26. In one embodiment, the base 62 of the deflation assembly 28 is placed against the pelvis between an anterior gluteal line and an iliac crest of the pelvis as illustrated. The base 62 is thus placed against the hard surface of the iliac crest and the outer peripheral rim 70 is easy to locate, which makes the activation area 72 easily palpatable.

Figure 9:
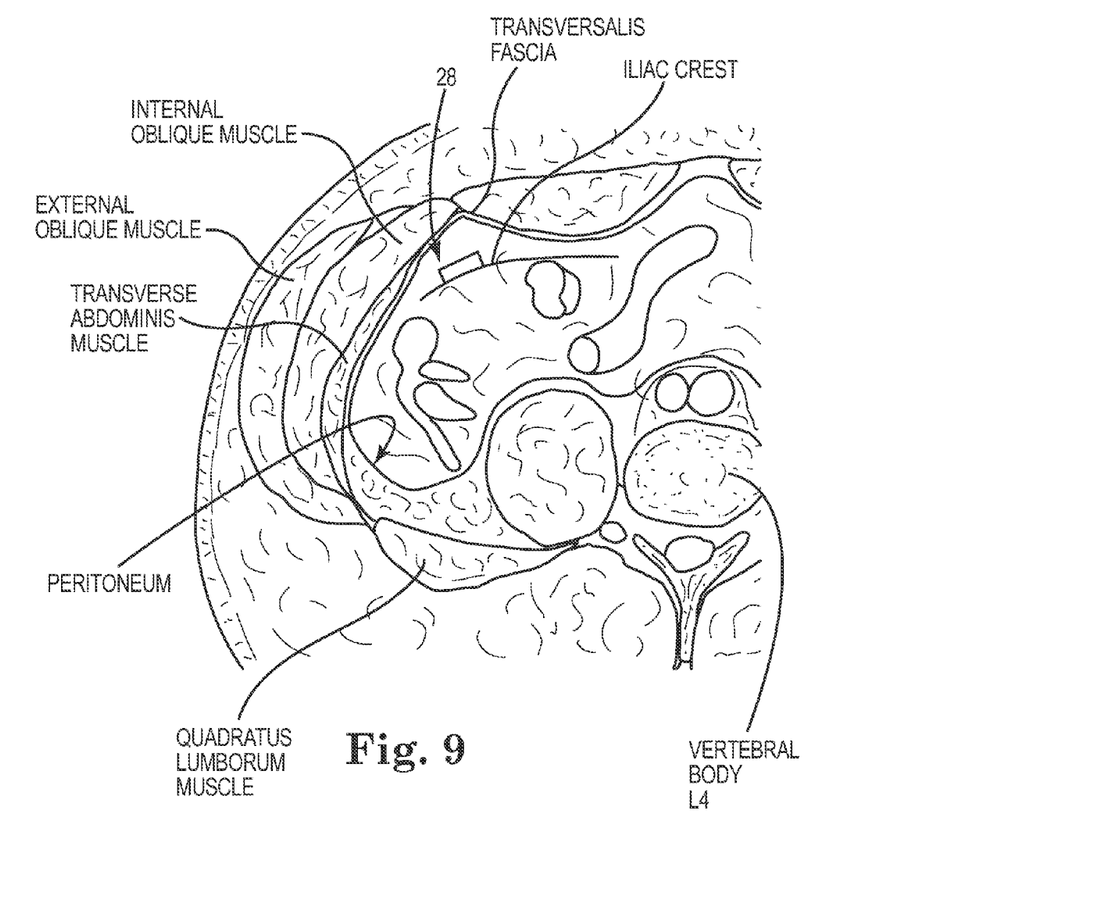
FIG. 9 is a top view of a pelvis showing the deflation assembly illustrated in FIG. 1 implanted between transversalis fascia and an exterior surface of the pelvis.

FIG. 9 is a top view of a pelvis showing the deflation assembly 28 implanted between transversalis fascia and an exterior surface of the pelvis. In particular, the deflation assembly 28 is located against the iliac crest of the pelvis and behind the transversalis fascia.

In one embodiment, the deflation assembly 28 is implanted behind a puborectalis muscle of the patient.

Embodiments thus provide implantation of a deflation assembly such that the outer peripheral rim 70 is distal the pelvis.

Figures 10A, 10B:
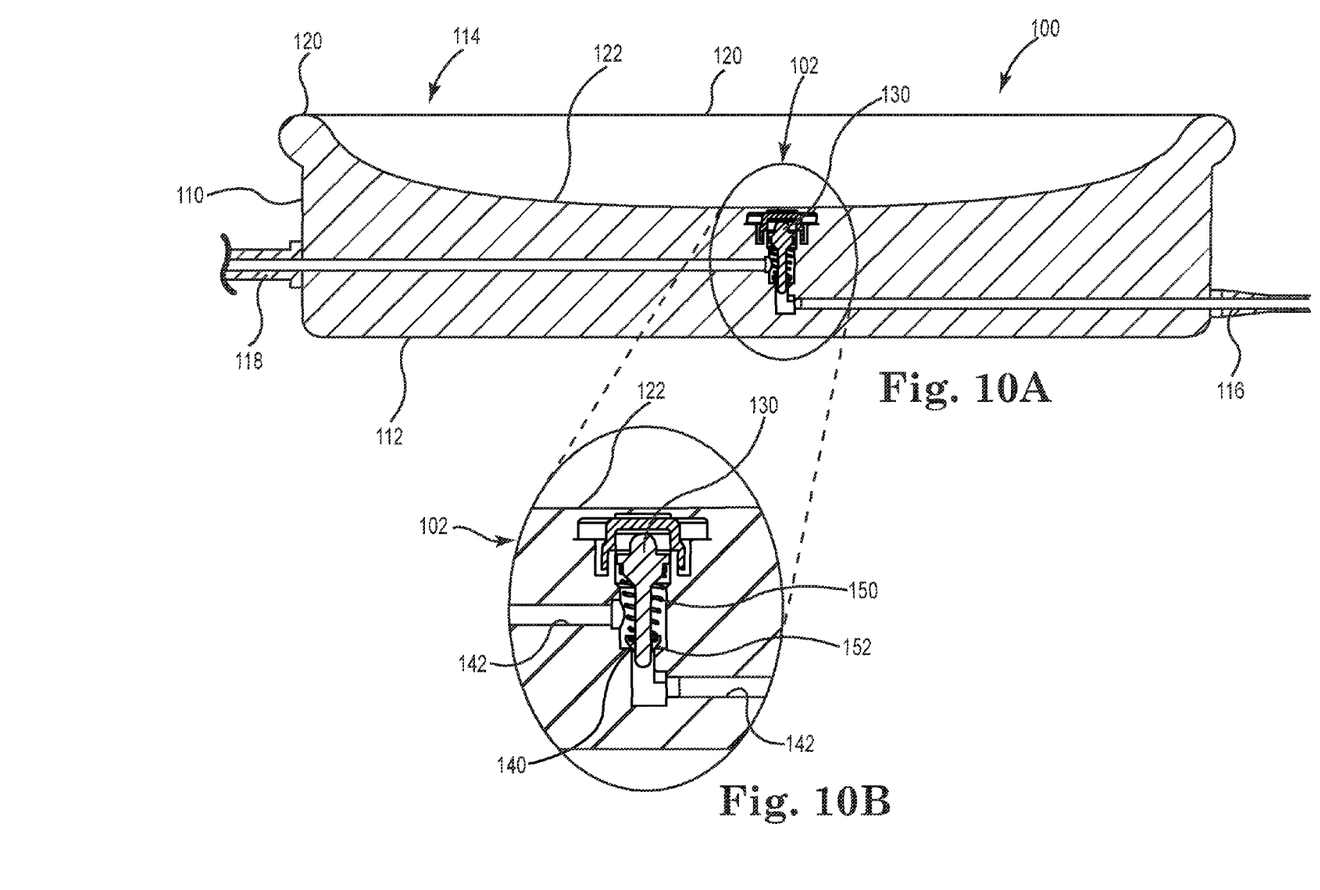
FIG. 10A is a cross-sectional view of one embodiment of a penile prosthetic deflation assembly.
FIG. 10B is a cross-sectional view of one embodiment of a valve assembly of the deflation assembly illustrated in FIG. 10A.

FIG. 10A is a cross-sectional view of one embodiment of a penile prosthetic deflation assembly 100 and FIG. 10B is a cross-sectional view of a valve assembly 102 of the deflation assembly 100. The deflation assembly 100 is operable with the kind of prosthetic described above, and is for example connected between the reservoir 24 and the pump 26 (FIGS. 1 and 6) to operate the penile implant 22.

The deflation assembly 100 includes a side surface 110 extending between a base 112 and activation surface 114. In one embodiment, the side surface 110 includes an inlet port 116 that communicates with the reservoir 24 and an outlet port 118 that communicates the penile implant 22 (FIG. 1). The activation surface 114 includes an outer peripheral rim 120 surrounding an activation area 122. The activation area 122 is recessed in a concave configuration relative to the outer peripheral rim 120 such that the outer peripheral rim 120 defines a maxima of the activation surface 114.

In one embodiment, the deflation assembly 100 encloses a stem valve 130 of the valve assembly 102 that is located between the inlet port 116 and the outlet port 118. The stem valve 130 is provided to selectively restrict movement of the fluid from the penile implant 22 to the reservoir 24 (FIG. 1) when the penile implant 22 is erect. The activation surface 114, and in particular the activation area 122, is operable to displace the valve 130 to allow movement of the fluid from the penile implant 22 back to the reservoir 24 to return the penile implant 22 to a flaccid state.

In one embodiment, the activation area 122 is movable toward the base 112 to move a position of the valve 130. In one embodiment, the outer peripheral rim 120 is substantially immovable and provides a hard, easily palpatable surface accessible by the user.

FIG. 10B illustrates one embodiment in which the stem valve 130 is shaped as a prong that extends from the activation area 122 toward the base 112 and is movable and so configured to displace an interface 140 between the valve 130 and a flow path 142 in which the valve 130 is seated. In one embodiment, the stem valve 130 includes a spring 150 that biases a check valve 152 into engagement with the interface 140.

With additional reference to FIG. 1, repeated squeezing of the pump 26 causes fluid to be drawn from the reservoir 24 through the inlet port 116 (FIG. 10A), which displaces the check valve 152 and compresses the spring 150, to move the check valve 152 off of the interface 140 to allow the fluid to flow through the flow path 142, out of the outlet port 118, and into to the implant 22.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An implantable medical device comprising:
an inflatable member;
a reservoir;
a pump attachable between the inflatable member and the reservoir and operable to move fluid from the reservoir to inflate the inflatable member; and
a deflation assembly attachable between the pump and the reservoir, the deflation assembly comprising:
a valve that selectively restricts movement of the fluid from the inflatable member to the reservoir,
a base and an activation surface opposite the base, the activation surface including an outer peripheral rim surrounding a pad that is movable to displace the valve to allow the fluid to flow from the inflatable member to the reservoir;
wherein the pad is recessed relative to the outer peripheral rim such that the outer peripheral rim defines a maxima of the activation surface.

2. The implantable medical device of claim 1, wherein the deflation assembly is separate from the reservoir and separate from the pump.

3. The implantable medical device of claim 1, wherein the pad is recessed in a concave configuration relative to the outer peripheral rim.

4. The implantable medical device of claim 1, wherein the pad is a diaphragm connected to the outer peripheral rim.

5. The implantable medical device of claim 1, wherein the valve is a ball valve.

6. The implantable medical device of claim 1, wherein the valve is a stem valve having a prong that extends from the pad toward the base of the deflation assembly, the prong movable and so configured to displace an interface between the valve and a flow path in which the valve is seated.

7. The implantable medical device of claim 1, wherein the outer peripheral rim is rigid and so configured to allow a user to palpate the pad through skin.

8. The implantable medical device of claim 1, wherein the base of the deflation assembly is a lower surface and the activation surface is an upper surface and the deflation assembly further comprises a side surface extending between the lower surface and the upper surface, the side surface including an inlet port communicating with the reservoir and an outlet port communicating with the inflatable member.

9. The implantable medical device of claim 8, wherein the activation surface includes a length and a width, and the length of the activation surface is larger than a height of the side surface extending between the lower surface and the upper surface.

10. The implantable medical device of claim 8, wherein the activation surface includes a length and a width, and the width of the activation surface is larger than a height of the side surface extending between the lower surface and the upper surface.

11. The implantable medical device of claim 8, wherein the activation surface includes a length and a width, and the length and the width are each larger than a height of the side surface extending between the lower surface and the upper surface.

12. The implantable medical device of claim 1, wherein the pad is movable toward the base and the outer peripheral rim is substantially immovable.

13. An implantable medical device comprising:
an inflatable member;
a reservoir;
a pump connectable between the inflatable member and the reservoir and operable to move fluid from the reservoir to the inflatable member to inflate the inflatable member; and
a deflation assembly separate from the reservoir and separate from the pump and connectable between the pump and the reservoir, the deflation assembly enclosing a valve that selectively restricts movement of the fluid from the inflatable member to the reservoir;
wherein the deflation assembly comprises a base and an activation surface opposite the base, the activation surface including a central activation area that is recessed in a concave configuration relative to an outer peripheral rim such that the central activation area is located between the outer peripheral rim and the base; and
wherein the activation surface is movable to displace the valve to allow movement of the fluid from the inflatable member to the reservoir.

14. The implantable medical device of claim 13, wherein the activation area is movable toward the base and the outer peripheral rim is substantially immovable.

15. The implantable medical device of claim 13, wherein the outer peripheral rim defines a maxima of the activation surface.

16. An implantable medical device comprising:
an inflatable member;
a reservoir configured to retain a fluid operable to inflate the inflatable member;
a pump connectable between the inflatable member and the reservoir and operable to move the fluid from the reservoir to the inflatable member to inflate the inflatable member; and
a deflation assembly separate from the reservoir and separate from the pump and connectable between the pump and the reservoir, the deflation assembly enclosing a valve that selectively restricts movement of the fluid from the inflatable member to the reservoir, and the deflation assembly including a base and an activation surface opposite the base, the activation surface including a central pad that is recessed in a concave configuration relative to an outer peripheral rim; and
means for moving the valve to allow movement of the fluid from the inflatable member to the reservoir.

17. The implantable medical device of claim 16, wherein the valve is a ball valve.

18. The implantable medical device of claim 16, wherein the valve is a stem valve.

19. The implantable medical device of claim 16, wherein an entirety of the pad is recessed relative to the outer peripheral rim such that the outer peripheral rim defines a maxima of the activation surface.

* * * * *